United States Patent [19]

Hammond

[11] Patent Number: 5,376,390
[45] Date of Patent: Dec. 27, 1994

[54] STABILIZING RICE BRAN AND RICE BRAN PRODUCTS

[75] Inventor: Neal A. Hammond, Cordova, Tenn.

[73] Assignee: Bran-Tec, Inc., Baton Rouge, La.

[21] Appl. No.: 179,078

[22] Filed: Jan. 10, 1994

Related U.S. Application Data

[62] Division of Ser. No. 975,527, Nov. 12, 1992, Pat. No. 5,292,537.

[51] Int. Cl.$^5$ .......................... A23C 9/12; C12N 9/96
[52] U.S. Cl. ........................................ 426/44; 426/18; 426/19; 426/28; 426/33; 426/320; 426/321; 426/330; 426/330.6; 426/391; 426/417; 426/446; 426/619; 426/654
[58] Field of Search ...................... 426/44, 18, 19, 28, 426/33, 320, 321, 330, 330.6, 391, 417, 446, 619, 654; 435/188

[56] References Cited

U.S. PATENT DOCUMENTS

| | | | |
|---|---|---|---|
| 2,585,978 | 2/1952 | Van Atta | 426/461 |
| 2,853,388 | 9/1958 | Kiely et al. | 426/18 |
| 5,041,245 | 8/1991 | Benado et al. | 554/10 |
| 5,153,019 | 10/1992 | Hammond | 426/590 |
| 5,166,388 | 11/1992 | Sawai et al. | 558/161 |
| 5,209,940 | 5/1993 | Champagne et al. | 426/320 |
| 5,292,537 | 3/1994 | Hammond | 426/44 |

Primary Examiner—Herbert J. Lilling
Attorney, Agent, or Firm—Grace J. Fishel

[57] ABSTRACT

A process for stabilizing rice bran containing protein and a naturally occurring lipase enzyme that causes rancidity. The rice bran is treated with an antilipase enzyme, preferably a nonspecific protease of plant or fungal origin. Treatment with the antilipase enzyme stabilizes the rice bran against rancidity without denaturing the protein. Stabilized rice bran has food and industrial utility and can be processed by a sequence of steps including wet milling and microfiltration into a variety of other products also having food and industrial utility. In some instances depending on the product, it is not necessary stabilize the rice bran before wet milling and microfiltration.

8 Claims, 3 Drawing Sheets

STABILIZING RICE BRAN AND RICE BRAN PRODUCTS

This is a division, of application Ser. No. 07/975,527, Nov. 12, 1992, now U.S. Pat. No. 5,292,537.

The present invention relates to a method for enzymatically stabilizing rice bran and to products produced from stabilized and unstabilized rice bran, included among which is a rice bran milk-replacer.

BACKGROUND OF THE INVENTION

When harvested from the field, rice is in the form of paddy or rough rice, where the kernel is enveloped by a rice hull. After being dried, rice for human consumption is first milled to remove the hull, yielding brown rice. In a second stage of milling, the outer brown layer is removed from the rice kernel to yield polished or white rice. Depending on the milling techniques, rice bran may include part of the germ and it may also be mixed with part of the hull.

The composition of rice bran (in percent by weight) is generally 11–13% of water, 18–21% of crude fat and oil, 14–16% crude protein, 8–10% of crude fiber, 9–12% of ash and 33–36% of carbohydrate. Rice bran has naturally occurring lipases that hydrolyze the oil into glycerol and free fatty acids which give the product a rancid smell and taste. Under normal milling conditions (ambient temperatures above freezing), rice bran will degrade in approximately six hours into an unpalatable material which is not suitable as a human food. Because of the problem with rancidity, most rice bran is used as feed for animals or as fertilizer or fuel.

The oil from rice bran is sometimes extracted for use as human food. Because of the lipases, most extractions are carried out close to the growing areas in small capacity rice mills. To obviate this problem, others have found that naturally occurring lipases can be deactivated by heating the rice bran for a snort period of time, as for example by passing it through a high temperature high pressure extruder. The heat stabilizes the rice bran such that it can be transported to a central operation for extraction of the oil but the protein is denatured by the heat such that the rice bran is unfit for use in the manner of the present invention.

SUMMARY OF THE INVENTION

An important object of the present invention is to provide a process for stabilizing rice bran by deactivating naturally occurring lipases without denaturing the rice bran's protein or otherwise altering its physical or chemical properties. The process may be advantageously applied to the rice bran in conjunction with milling on a local basis close to the rice growing fields with the stabilized rice bran being transported to a centralized facility for further processing. Another object is to provide a process which realizes the full nutritional potential of rice bran in a number of useful products including a rice bran milk-replacer. Other objects and features of the invention will be in part apparent and in part pointed out hereinafter.

In accordance with the invention, rice bran containing protein and having a naturally occurring lipase enzyme that causes rancidity is stabilized without denaturing the protein. An antilipase enzyme is selected which inactivates the naturally occurring lipase enzyme in the rice bran. The rice bran is mixed with water and with the antilipase enzyme. The antilipase enzyme is provided in an amount effective to substantially inactivate the lipase enzyme in a period of time that is a function of the amount of water present in the mix. At the end of the inactivation period, the rice bran is stabilized against rancidity without denaturing the protein. The wet stabilized rice bran can be dried or processed into other products for use in food or industry.

The wet stabilized rice bran can be wet milled (sometimes with pH adjustment) and the soluble dietary fiber separated as a liquid phase from the insoluble dietary fiber. The protein and other nutritional components of the rice bran such as starch, minerals, vitamins and so forth pass mainly in the liquid phase. Optionally the starch in the liquid phase can be converted into dextrins and dextroses by application of acid, heat and/or amylases. The liquid phase is microfiltered (with a molecular weight cut-off of 100,000 or greater) and then ultrafiltered (with a molecular weight cut-off of 10,000 or greater) to produce various products having food or industrial utility. Depending on the product to be produced from rice bran, in some instances, it is not necessary to stabilize the rice bran before it is wet milled and processed as described above.

The invention summarized above comprises the methods and products hereinafter described, the scope of the invention being indicated by the subjoined claims.

BRIEF DESCRIPTION OF THE DRAWINGS

In the accompanying drawings, in which several of various possible embodiments of the invention are illustrated.

DETAILED DESCRIPTION OF THE INVENTION

The present invention is concerned with a series of processing steps by which a number of novel products are obtained from rice bran. It starts with freshly milled rice bran which is provided as a flour preferably ground to the point that all of the material will pass through a 40 mesh screen. The rice bran has a naturally occurring lipase which tends to hydrolyze the oil in the rice bran into glycerol and fatty acids. Suitable starting materials include recently milled (unhydrolyzed) full-fat rice bran, low-fat rice bran, defatted rice bran and so forth. Low-fat rice bran and defatted rice bran are derived from full-fat rice bran by solvent extraction or the like. Full-fat rice bran has a fat content of about 14–18% by weight and low fat and defatted rice bran have about 3–14% and less than 3% fat, respectively, on a weight basis.

Figure 1:
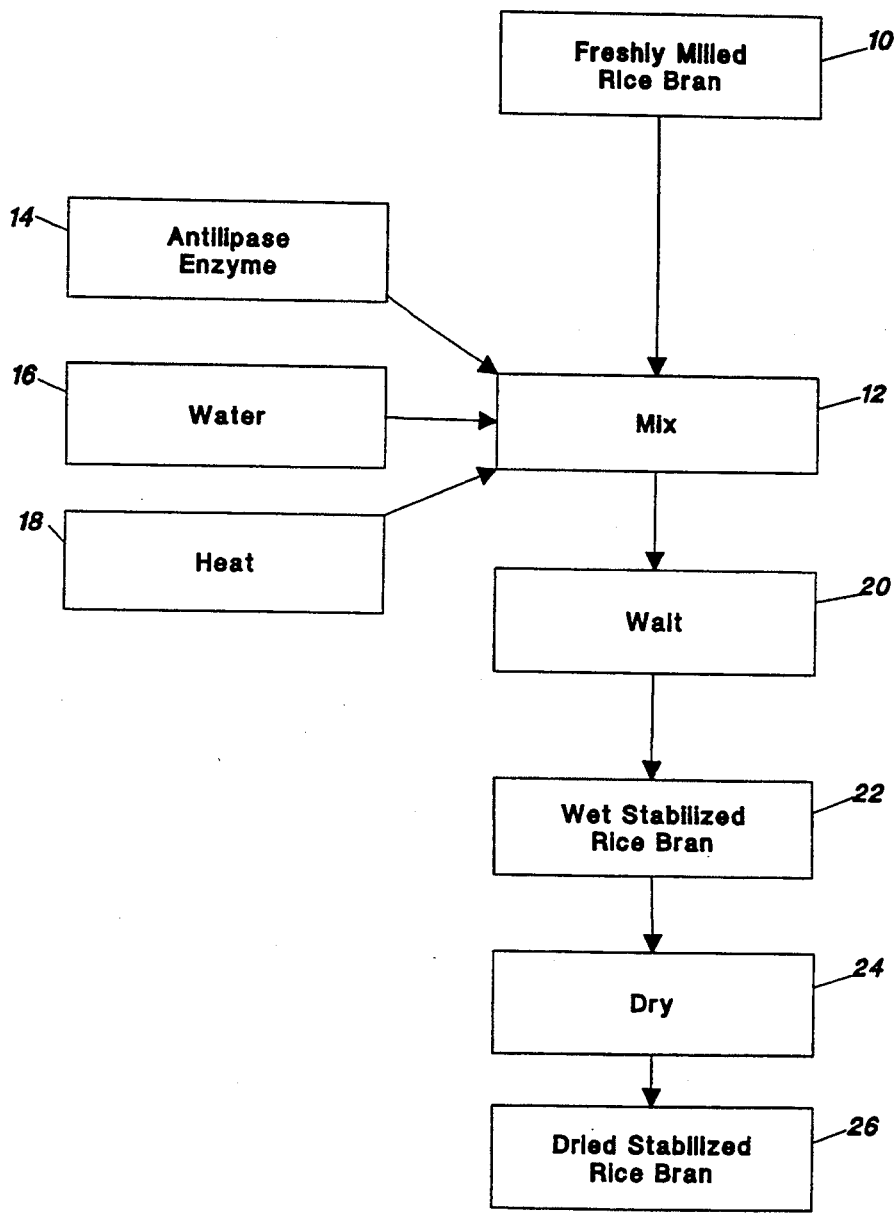
FIG. 1 is a schematic flow sheet of a method for stabilizing rice bran in accordance with the present invention.

As described in the schematic flow sheet shown in FIG. 1, a quantity of rice bran 10 is placed in a mixer 12. An inactivating enzyme 14 is selected to inactivate the naturally occurring lipase in the rice bran. Suitable materials for this purpose are known to include nonspecific proteases of plant and fungal origin. For example, papain, an enzyme naturally occurring in papaya fruit, and bromelin, an enzyme naturally occurring in pineapples, function as suitable antilipase enzymes 14 when used as described below. Enzeco Fungal Protease brand concentrate, an enzyme fermented from various fungi, also functions as an antilipase enzyme. Enzeco Fungal Protease brand concentrate is a commercially available product from Enzyme Development Corporation located in New York City, N.Y. All the aforementioned antilipase enzymes appear to work with substantially the same degree of efficiency. Proteases of bacterial and animal origin (such as pancreatic) may also be useful and mixtures of antilipase enzymes are also contemplated.

In general, freshly milled rice bran 10 has a water content of 20% by weight or less, in general about 10%. As shown in FIG. 1, prior to or concurrent with enzymatic treatment according to the present invention, the water content of the rice bran is increased to permit the activity of the antilipase enzymes mentioned above, all of which function in an aqueous or hydrated environment. Additional water above the threshold amount needed to activate the antilipase enzyme in general increases the speed of inactivation. For example, when water is added to the fresh rice bran in a ratio of 1:10 based on weight, the stabilization process takes approximately 24 hours to complete, whereas when the water to rice bran ratio is 5:1 based on weight, the process will be completed in approximately five minutes. Rice bran 10 does not become unpalatable even when the stabilization process takes as long as 24 hours to complete. While additional water increases the speed with which the rice bran is stabilized, excessive amounts of water should be avoided as it must be removed later and increases the processing costs.

With continuing reference to FIG. 1, selected antilipase enzyme 14 is added to a quantity of water 16 sufficient to wet rice bran 10 and activate the enzyme. Water 16 is preferably preheated at 18 with steam or the like. Antilipase enzyme 14 is added in an amount effective to substantially inactivate the lipase in a selected time that is dependent, as described above, on the amount of water used to wet the rice bran. For this purpose, antilipase enzyme 14 is preferably employed at levels of from about 0.01% to about 0.1% by weight. After the antilipase enzyme is added, the mixture is maintained, preferably with continued mixing, at a temperature of about 20 degrees C. to about 50 degrees C. for a waiting period 20 sufficient for the antilipase enzyme to inactivate substantially all of the naturally occurring lipase in the rice bran. Within the above-mentioned ranges, waiting time 20 is shorter at higher temperatures and with higher levels of antilipase enzyme 14. At the end of period 20, rice bran 10 has been processed into a wet stabilized rice bran 22.

As shown in FIG. 1, wet stabilized rice bran can be dried 24 by air drying, oven drying, vacuum drying, freeze drying or the like to produce a dried product 26. The dried product has a moisture content preferably in the range from about 6% to about 10% by weight and can be stored for long periods of time without deterioration. Dried stabilized rice bran product 26 can be rewetted for further processing as shown in FIGS. 2 and 3 or used as an ingredient in various food products.

Figure 2:
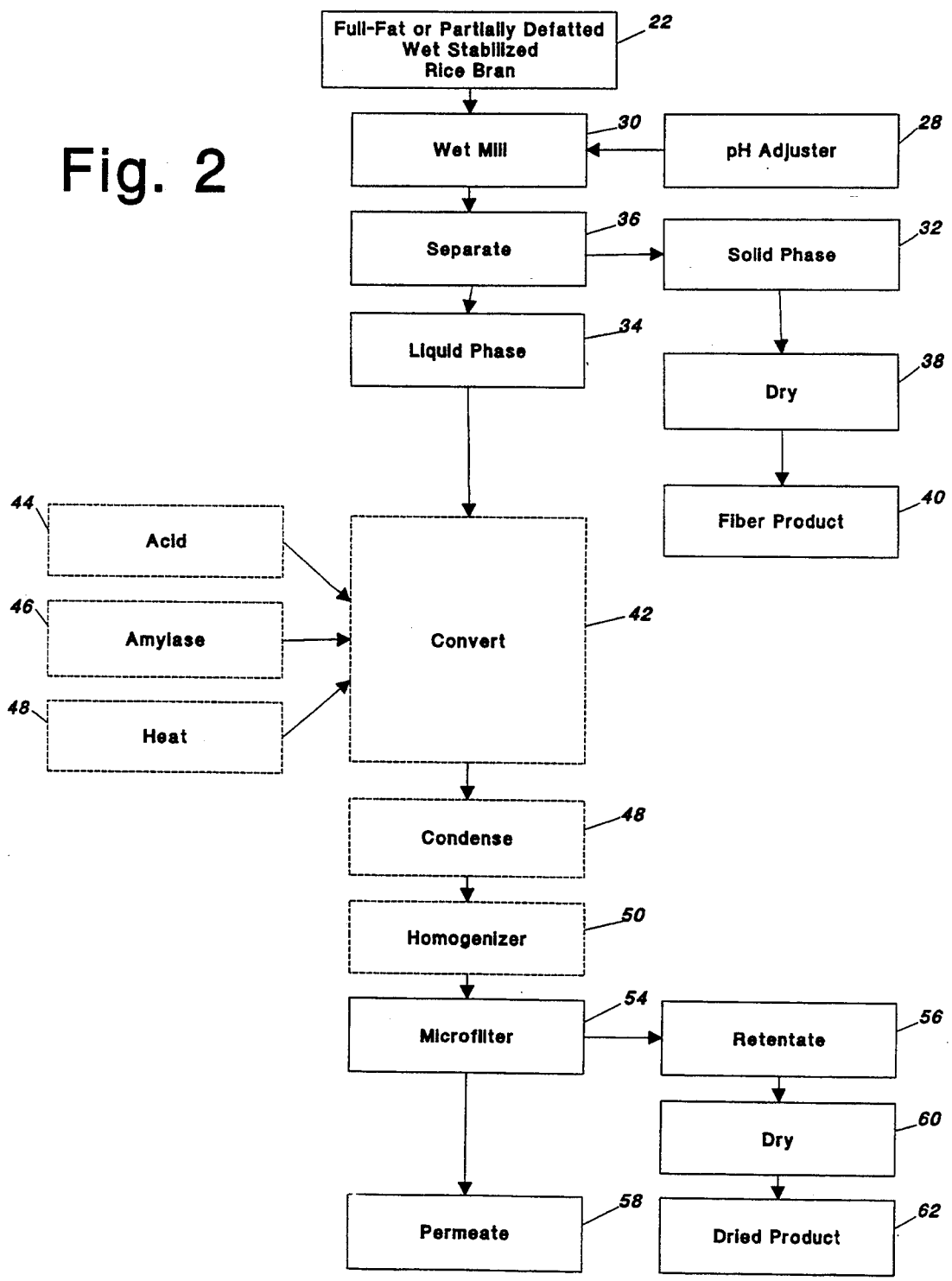
FIG. 2 is a schematic flow sheet showing further processing of a stabilized full-fat or partially defatted rice bran in accordance with the present invention to produce, inter alia, a milk-replacer; and, FIG. 3 is a schematic flow sheet showing further processing of a stabilized rice bran in accordance with the present invention to produce various products other than a milk-replacer.

Wet stabilized rice bran 22 (or rewetted dried rice bran 26) can be further processed as shown in FIG. 2 when it is prepared from rice bran 10 which is full-fatted or only partially defatted. Wet stabilized rice bran 22 can be further processed as shown in FIG. 3 when it is prepared from rice bran 10 whether it is defatted or not, the nature of the products, however, depend on the fat content.

Figure 3:
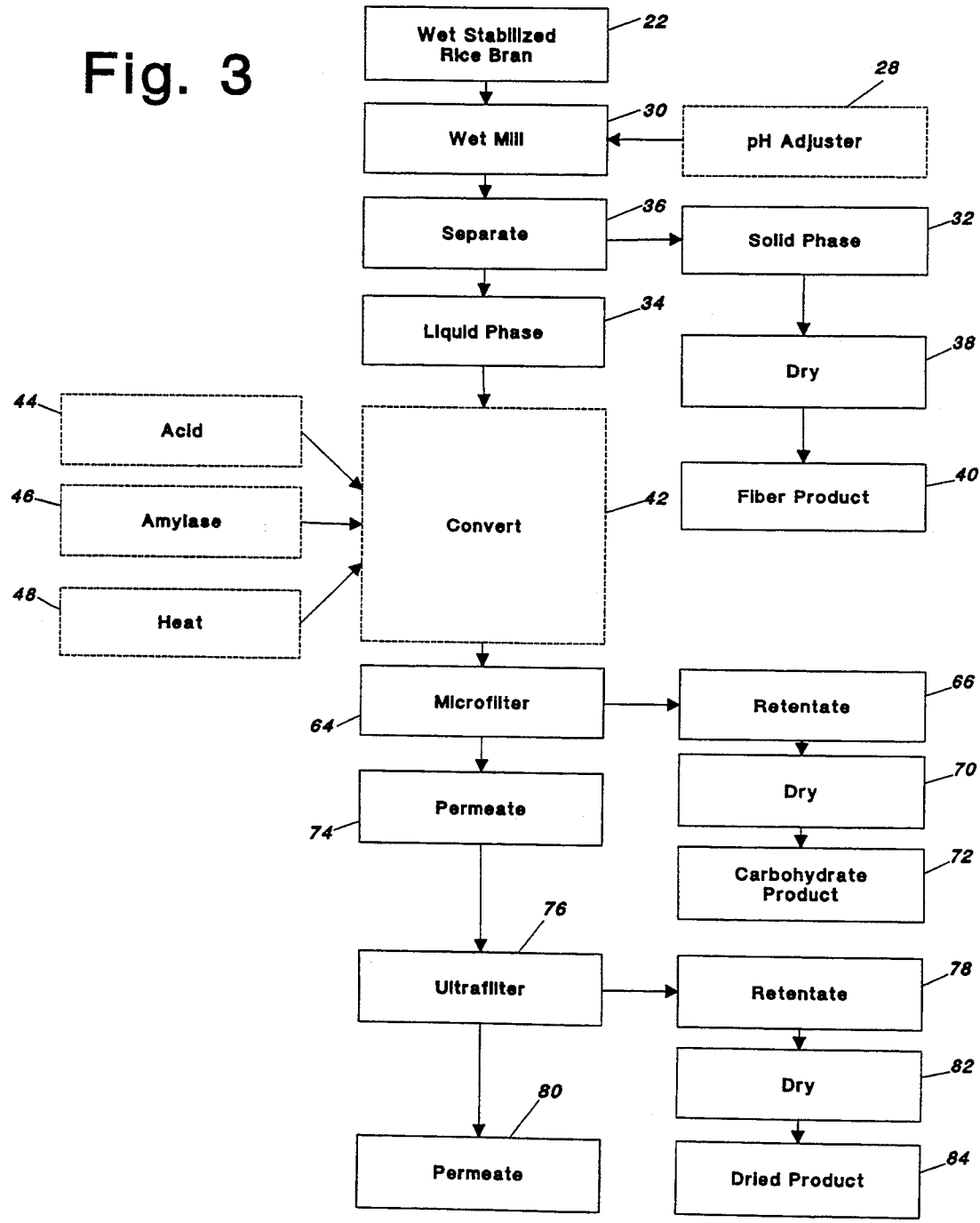

As a first step of further processing in both FIGS. 2 and 3, the insoluble dietary fiber present in wet stabilized rice bran 22 must be separated from the water soluble dietary fiber. Soluble dietary fiber is considered beneficial but insoluble dietary fiber tends to accelerate the passage of the rice bran through the human digestive tract so that only a small nutritive contribution is realized.

The pH of wet stabilized rice bran 22 affects the way in which the protein is partitioned when the insoluble dietary fiber is separated from the soluble dietary fiber. More particularly, proteins are more soluble when the pH is on the basic side. For that reason, it is preferred that the pH of wet stabilized rice bran 24 be adjusted with a pH adjuster 28 so that the pH is from about 7.5 to about 12. In this range, most of the proteins stay in water solution and are not denatured. Suitable food grade bases for pH adjuster 28 include calcium hydroxide, sodium hydroxide, potassium hydroxide, ammonium hydroxide and so forth. Calcium hydroxide is preferred for nutritional reasons since it is a source of additional calcium. If more protein is desired in the insoluble dietary fiber, the pH of wet stabilized rice bran 22 is adjusted to neutral or acidic. In which case, pH adjuster 28 is a food grade acid, suitable ones of which are illustrated below. The exact effect of the pH of the wet stabilized rice bran and amount of protein in the insoluble dietary fiber can be determined empirically.

The pH-adjusted, wet stabilized rice bran 22 is wet milled 30 such as in a mixer/grinder into a slurry consisting of a finely ground solid phase 32 containing the insoluble dietary fiber and a liquid phase 34. The protein and other nutritional components of the rice bran such as starch, minerals, vitamins and so forth pass mainly with the soluble dietary fiber into liquid phase 34. The solid phase is separated 36 from the liquid phase by means of a decanter centrifuge or the like. Solid phase 32 can then be dried 38 such as in a spray dryer into a dried fiber product 40.

After the insoluble dietary fiber (fiber product 40) has been separated from liquid phase 34, the liquid phase can be processed into a number of other products. The nature of the other products depend on whether liquid phase 34 was derived from a full-fat, partially defatted or fully defatted rice bran 10. The products also depend on whether the starch in liquid phase 34 is converted into simpler carbohydrates and on the amount of conversion. Subsequent filtration steps also affect the nature of the products as more particularly discussed below.

When liquid phase 34 is derived from a full-fat or only partially defatted rice bran 10, the liquid phase can be further processed into a milk-replacer as shown in FIG. 2. When liquid phase 34 is made from a full-fat rice bran 10, a whole-milk milk-replacer is produced, whereas a partially defatted rice bran 10 provides a low-fat milk-replacer. For this purpose, it is necessary that the starch in liquid phase 34 be converted 42 into dextrins and dextroses. This can be accomplished by treating liquid phase 34 with acid, heat or enzymes or some combination thereof.

In the production of a milk-replacer as shown in FIG. 2, it is preferred that the pH of liquid phase 34 be adjusted to about 5.5 to 7.0 with a food grade acid 44. In this range, the proteins are still soluble and not coagulated and the end products are more palatable for human consumption. The minerals and phytin are made more soluble. Mineral acids such as hydrochloric acid and sulfuric acid or organic acids such as citric acid, fumaric acid, maleic acid or acetic acid and so forth may be used to achieve the desired pH.

Following pH adjustment, an amylase 46 is added to liquid phase 34 to enzymatically digest the starch into dextrins. Conversion is further promoted by heating the mixture to a temperature in the range of about 50 degrees C. to about 60 degrees C. An amyloglucosidase may also be added to aid in the conversion of the dextrins into glucoses. Acceptable results have been obtained when the enzymatic digestion is carried out with from about 0.1 l to about 1.0 l of amylase per ton of stabilized rice bran 26. When amyloglucosidase is used, it is preferably present at a level of about 0.1 l to about 1.0 l per ton. Amylase is commercially available as TERMAMYL 1 from Novo Nordisk of Copenhagen, Denmark and amyloglucosidase is commercially available as AMG from Novo Nordisk.

Conversion is allowed to continue until about 80% to about 100% by weight of the starch has been digested into dextrins and glucoses that will pass through a 100,000 molecular weight filter. The time necessary for this to occur varies from about 15 minutes to about 4 hours depending upon the pH of liquid phase 34, the temperature and the amount of amylase (and amyloglucosidase, if present). Preferably, conversion occurs in about 15 minutes to about 1 hour.

After the desired extent of conversion is completed, liquid phase 34 may be condensed 48 by removal of some of the water. This may be accomplished by passing liquid phase 34 through a vacuum evaporator where from about 20% to about 60% by weight of the water is removed. The fat may then be homogenized 50, if desired, by passing liquid phase 34 through a homogenizer.

With continuing reference to FIG. 2, after conversion 42 (and condensation 48 and homogenization 50, if any), liquid phase 34 is filtered through a filter having a particle size or molecular weight cut-off such that a retentate 56 contains proteins, fats and carbohydrate of a selected molecular weight and higher and a permeate 58 contains phytin, minerals and vitamins, along with proteins, fats and sugars which pass through the filter. Retentate 56 may be dried 60 in a spray drier or the like into a dried product 62.

Filters suitable for filtering liquid phase 34 are typically membrane filters, sometimes referred to as hollow fibers, spiral wound and ceramic filters. A detailed discussion of microfiltration and ultrafiltration means can be found in "*Ultrafiltration Handbook*" by M. Cheryan, Technomic Publishing Co., 1986.

As shown in FIG. 2, liquid phase 34 is passed through a microfilter with a molecular weight cut-off of about 250,000 to about 100,000, more preferably a molecular weight cut-off of about 100,000.

If products other than a milk-replacer are wanted, liquid phase 34 can be processed as shown in FIG. 3. The process shown in FIG. 3 can be used on wet stabilized rice bran 22 derived from defatted as well as full-fat and partially defatted rice bran. The process is identical to that shown in FIG. 2 down to the point that the starches in liquid phase 34 are converted with acid 44, heat 48 and amylase 46. In this instance, conversion is stopped, preferably after a period of about 10 minutes to 30 minutes, or when less than about 80% by weight of the starch has been digested into simpler carbohydrates that will pass through a 100,000 molecular weight filter.

Liquid phase 34 is passed through a microfilter 64 (preferably a 100,000 molecular weight microfilter) such that a retentate 66 contains carbohydrates having a molecular weight of 100,000 or higher. Retentate 66 can be dried 70 such as in a spray drier to yield a slow-release carbohydrate product 72.

Permeate 74 from the microfiltration step can be further passed through an ultrafilter 76 with a molecular weight cut-off of about 20,000 to about 10,000, preferably about 15,000 to about 10,000, and more preferably about 10,000. A retentate 78 on ultrafilter 76 contains proteins and simple sugars having a molecular weight of 10,000 and higher and a permeate 80 contains phytin, minerals and vitamins, along with any proteins and sugars which pass through ultrafilter 76. Retentate 78 can be dried 82 in a spray drier or the like into a dried product 84.

Rice products, unlike soy products, are generally non-allergenic. Hence it is anticipated that wet stabilized rice bran 22 and dried products 26, 40, 62, 72 and 84 and liquid products 58 and 80 have a similar characteristic. For example, dried product 62 can be used as a hypoallergenic milk-replacer either in its dried form or reconstituted to a liquid consistency. When reconstituted, the solids content can be adjusted by the addition of water to yield a beverage very similar in appearance and taste to milk. Dried product 62 can also be used in a wide variety of food formulations as a replacement for milk and sugar solids. Dried product 84 cannot be used as a milk-replacer but it is useful for other purposes in food products. Dried product 40 can be used as fiber in health foods and dried product 72 is a good source of slow-release carbohydrates. Liquid products 58 and 80 are rich in minerals and phytin and may be used, for example, as an isotonic sports drink.

Depending on the product to be produced, in some instances it is not necessary to stabilize the rice bran before the rice bran is wet milled as shown in FIGS. 2 and 3. In this instance, wet rice bran is substituted for wet stabilized rice bran 22. Products, like permeate 58 and permeate 80, contain very little fat or oil so whether or not the rice bran is stabilized is of little importance. Products like retentate 66, on the other hand, contain fat or oil. If retentate 66 is intended for use, for example in the cosmetic and pharmaceutical industry, the presence of active lipase may be advantageous. In this instance, the lipases may be used to partially hydrolyze the triglycerides into mono- and diglycerides and are then deactivated by the addition of an antilipase enzyme or the application of heat. Mono- and diglycerides are useful as emulsifiers.

The following examples illustrate the invention.

EXAMPLE 1

Enzymatic Stabilization of Fresh Rice Bran

A full-fat dried stabilized rice bran 26 was prepared as shown in FIG. 1. To thirty pounds of water 16, five ounces of Enzeco Fungal Protease brand concentrate 14 was added and thoroughly mixed. The aqueous solution was added to 300 pounds of fresh full-fat rice bran 10 and mixed in a planetary mixer for 20 minutes (mixing step 12). The mixture was allowed to work for twenty minutes (waiting time 20) at 85 degrees F. (heating step 18). The wet stabilized rice bran 22 was then dried to 6% by weight in a forced air oven (drying step 24).

The resulting dried stabilized rice bran 26 had a fatty acid content of 1.82% of total oil content after three weeks of storage. The free fatty acid content of unhydrolyzed rice bran is 0.28% by weight. The normal free fatty acid content in unstabilized rice bran at the same moisture and temperature varies from 35% to 55% of total oil content. The reduction in free fatty acid present in the product after three weeks of storage demonstrates that the lipase enzyme had been deactivated and that the resulting dried stabilized rice bran 26 should have a long shelf life without deterioration.

EXAMPLE 2

Aqueous Extraction of Full-Fat Rice Bran and Production of Whole Milk Replacer The dried stabilized rice bran 26 prepared in Example 1 by the process shown in FIG. 1 was further processed as shown in FIG. 2. 1,250 pounds of water was heated to 82 degrees F. and 250 pounds of full-fat dried stabilized rice bran 26 were added to the water. The pH of the resultant wet stabilized rice bran 22 was 6.7. The pH was adjusted to 9.15 by the addition of 1,000 ml of 50% sodium hydroxide (pH adjuster 28).

The product was passed through an in-line mixer/grinder (wet mill step 30) and then through a decanter centrifuge (separation step 36). The liquid phase 34 was put through the decanter centrifuge twice and then the pH was adjusted from 9.1 to 6.1 with the addition of hydrochloric acid (addition of acid step 44). The solid phase 32 was spray dried (drying step 38) after it was washed with water.

BioCon brand amylase enzyme (addition of amylase step 46) was then added to convert (conversion step 42) the starch to simpler carbohydrates such as dextrins and glucoses. BioCon is a trademark of BioCon Systems Company in Louisville, Ken.

The product of the conversion went to a Contherm vacuum evaporator and was flashed to 85 degrees F. (condensation step 48). Solids after the vacuum evaporator were 7.5% by weight as measured by a Cenco moisture analyzer. Remaining liquid phase 34 was homogenized (homogenization step 50). The purpose of the homogenization step was to combine the fats and the proteins in the liquid. Homogenization typically occurs from 1,500 to 15,000 PSI. The first stage of homogenization occurred at 2,000 PSI and the second stage occurred at 500 PSI. The liquid then went through a 100,000 molecular weight filter (microfilter step 54). The system used a Polysulfone membrane. The retentate 56 was then spray dried to yield a total of 1.8 pounds of material from the chamber and 0.47 pounds from the cyclones.

The process described above produced the following three products:
1. Fiber product 40.
The analysis of the fiber product was:

| Protein | 19.58% |
| Fat | 19.69 |
| Fiber | 13.20 |
| Ash | 11.11 |
| Carbohydrates | 36.42 |

2. Whole-milk milk-replacer (dried product 62)
The proximate analysis of the milk replacer was:

| Protein | 26.6% |
| Fat | 26.6 |
| Carbohydrates | 36.2 |
| Moisture | 4.0 |
| Ash | 3.0 |
| Fiber | 3.6 |

3. Isotonic sports drink (permeate 58)

Permeate 58 is rich in phytic acid. Phytic acid comprises as much as 7% by weight of rice bran and at one time was considered an undesirable component. Now, however, phytic acid and its salts are considered to be one of the most profitable constituents. Phytic acid is an inositol phosphate and is used as a chelating agent and surfactant in the surface coating and metal industry. When phytic acid is hydrolyzed under certain conditions, it can be converted to inositol, a compound shown to be essential to growth and development. Inositol is used in vitamin mixes, food/feed additives, medicines and cosmetics. Permeate 58 is also rich in vitamins, particularly thiamin, riboflavin and niacin.

EXAMPLE 3

Aqueous Extraction of Low-Fat Rice Bran and Production of Low-Fat Milk Replacer Following the process shown in FIG. 2, three hundred pounds (136 kg) of low-fat (9% fat) dried stabilized rice bran 26 was mixed with 1,240 pounds (567 kg) of water. The pH initially was 6.3 and was increased to 9.35 by the addition of 140 ml of 50% sodium hydroxide (pH adjustment step 28 in FIG. 2). The mixture was wet milled (wet milling step 30) and then passed twice through a decanter centrifuge (separation step 36).

The pH of the liquid phase 34 was adjusted to 6.7 with hydrochloric acid (addition of acid step 44) and heated to 190–200 degrees F. (heating step 48) and held for 45 minutes while 100 ml of amylase (addition of amylase step 46) and some "Edlong", a natural masking flavor, were added.

The liquid phase 34 was then evaporated in a Contherm flashed to 85 degrees C. (condensation step 48). The product was then homogenized at 2,500 PSI, 2,000 PSI first stage and 500 PSI second stage (homogenization step 50). Liquid phase 34 was then microfiltered with a 100,000 molecular weight filter. The solids were 16% (refractometer) and weighed 115 pounds. Retentate 56 was spray dried (drying step 60).

The above process produced the following three products:
1. Fiber product 40

| Protein | 19.58 |
| Fat | 19.69 |
| Fiber | 13.20 |
| Ash | 11.11 |
| Carbohydrates | 36.42 |

The fiber product 40 of Example 3 is like the fiber product 40 of Example 2.

2. Low-fat milk replacer (dried product 62)
The low-fat milk replacer was a complex of proteins, carbohydrates and fats derived from partially defatted bran.

The proximate analysis was:

| | |
|---|---|
| Protein | 30.3% |
| Fat | 14.8 |
| Carbohydrates | 45.0 |
| Ash | 3.0 |
| Moisture | 4.0 |
| Fiber | 2.9 |

3. Permeate 58

The permeate from the 100,000 molecular weight microfilter provides an isotonic sports drink containing phytic acid, vitamins and minerals. Permeate 58 of Example 3 is like permeate 58 of Example 2.

EXAMPLE 4

Extraction of Phytin and Other Products

Using the process shown in FIG. 3, 50 pounds of stabilized rice bran 22 (from Example 1) were added to 40 gallons of water. This combination was mixed for 15 minutes (wet mill step 30) and then pumped to a rotating 80 mesh screen (separation step 36). A fiber-rich solid phase 32 and a liquid phase 34 were collected.

Twenty-four liters of liquid phase 34 were placed in a tank and pumped through an AMICON 0.1 micron hollow fiber microfiltration system 64. Pressures were 20 PSI inlet and 10 PSI outlet and the flow averaged 20 gallons per minute. Two liters (1) of retentate 66 and 22 l of permeate 74 were collected.

Permeate 74 was then filtered a second time through a 30,000 molecular weight cut-off ultrafilter 76. The protein content of retentate 78 was 1.0% by weight and the protein content of permeate 80 was 0.8% by weight.

EXAMPLE 5

This example was carried out exactly like Example 4 except that the 30,000 molecular weight cut-off ultrafilter 76 was replaced with a 10,000 molecular weight cut-off ultrafilter. The protein content of retentate 78 was 1.5% by weight and the protein content in permeate 80 was too low to measure. Permeate 80 of Example 5 is like permeate 58 in Examples 2 and 3.

In view of the above, it will be seen that the several objects of the invention are achieved and other advantageous results attained. As various changes could be made in the above methods and products without departing from the scope of the invention, it is intended that all matter contained in the above description or shown in the accompanying drawings shall be interpreted as illustrative and not in a limiting sense.

What is claimed is:

1. A stabilized rice bran made by a method for enzymatically stabilizing rice bran containing protein and having a naturally occurring lipase enzyme that causes rancidity comprising:
   (a) selecting an antilipase enzyme which inactivates the naturally occurring lipase enzyme in the rice bran;
   (b) mixing the rice bran with water and the antilipase enzyme, said antilipase enzyme being in an amount effective to substantially inactivate the lipase enzyme in a period of time that is dependent on the amount of water; and,
   (c) waiting the period of time for the inactivation to occur whereby a wet stabilized rice bran is produced without denaturing the protein.

2. The stabilized rice bran of claim 1 wherein the water is present in a water to rice bran ratio of about 1:10 to about 5:1 by weight.

3. The stabilized rice bran of claim 1 wherein the mixture of rice bran, water and antilipase enzyme is held at a temperature from about 20 degrees to about 50 degrees C. during the waiting period for inactivation to occur.

4. The stabilized rice bran of claim 1 wherein the antilipase enzyme is a nonspecific protease of plant, fungal, bacterial or animal origin.

5. The stabilized rice bran of claim 1 wherein the antilipase enzyme is selected from the group consisting of papain, bromelin and fungal protease.

6. The stabilized rice bran of claim 1 further comprising drying the wet stabilized rice bran to produce a dried stabilized rice bran.

7. A stabilized rice bran made by a method for enzymatically stabilizing rice bran containing protein and having a naturally occurring lipase enzyme that causes rancidity comprising:
   (a) selecting an antilipase enzyme which inactivates the naturally occurring lipase enzyme in the rice bran, said antilipase enzyme being a nonspecific plant protease or a nonspecific fungal protease;
   (b) mixing the rice bran with water in a ratio of about 1:10 to about 5:1 by weight and with the antilipase enzyme in an amount effective to substantially inactivate the lipase enzyme;
   (c) holding the mixture of rice bran, water and antilipase enzyme at a temperature from about 20 degrees C. to about 50 degrees C. while waiting the period of time for the inactivation to occur whereby a wet stabilized rice bran is produced without denaturing the protein.

8. The stabilized rice bran of claim 7 further comprising drying the wet stabilized rice bran to produce a dried stabilized rice bran.

* * * * *